US006287829B1

(12) United States Patent
Stütz de Raadt et al.

(10) Patent No.: US 6,287,829 B1
(45) Date of Patent: Sep. 11, 2001

(54) PROCESS FOR THE SELECTIVE ENZYMATIC HYDROXYLATION OF ALDEHYDES AND KETONES

(75) Inventors: Anna Stütz de Raadt, Graz; Irene Kopper, Innsbruck; Herfried Griengl, Graz; Markus Klingler, Markt Hartmannsdorf; Gerhart Braunegg, Graz, all of (AT)

(73) Assignee: DSM Fine Chemical Austria Nfg GmbH & Co KG, Linz (AT)

( * ) Notice: Subject to any disclaimer, the term of this patent is extended or adjusted under 35 U.S.C. 154(b) by 0 days.

(21) Appl. No.: 09/381,203
(22) PCT Filed: Mar. 13, 1998
(86) PCT No.: PCT/EP98/01467
§ 371 Date: Sep. 17, 1999
§ 102(e) Date: Sep. 17, 1999
(87) PCT Pub. No.: WO98/41647
PCT Pub. Date: Sep. 24, 1998

(30) Foreign Application Priority Data

Mar. 18, 1997 (AT) ........................................... 468/97

(51) Int. Cl.[7] ................ C12P 7/02; C07C 45/00
(52) U.S. Cl. .............. 435/155; 435/147; 435/148; 435/832; 568/343; 568/376; 568/379; 568/420; 568/626
(58) Field of Search ...................... 435/149, 147, 435/155, 132, 832, 874, 933; 568/338, 376, 379, 343, 420, 626

(56) References Cited

U.S. PATENT DOCUMENTS 5,360,724    11/1994    Matcham et al. .................... 435/128

OTHER PUBLICATIONS

*Chemical Abstract*, 125(1), Abstract No. 10221 (Jul. 1996).
De Raadt et al., *Tetrahedron: Asymmetry*, 7(2), 467–472 (1996).
De Raadt et al., *Tetrahedron: Asymmetry*, 7(2), 473–490 (1996).
De Raadt et al., *Tetrahedron: Asymmetry*, 7(2), 491–496 (1996).

*Primary Examiner*—Sreeni Padmanabhan
(74) *Attorney, Agent, or Firm*—Wenderoth, Lind & Ponack, L.L.P.

(57) ABSTRACT

A process for the selective enzymatic hydroxylation of aldehydes and ketones using chiral anchor-protective groups.

7 Claims, No Drawings

PROCESS FOR THE SELECTIVE ENZYMATIC HYDROXYLATION OF ALDEHYDES AND KETONES

This is the U.S. National Stage Application of PCT/EP98/01467, filed Mar. 13, 1998.

The present invention relates to a process for the selective hydroxylation of aldehydes. and ketones using enzymes or microorganisms

TECHNOLOGICAL BACKGROUND

Hydroxylated aldehydes and ketones are of great industrial importance as synthesis intermediates. Thus, DE 36 22 839 discloses the synthesis, using hydroxylated ketones, of compounds having cardiac activity.

WO 86/07611 discloses the synthesis of 4-hydroxycyclopent-2-en-1-one and 3-hydroxycyclopentanone. These compounds are used in the preparation of prostaglandins.

A further area of application is the preparation of compounds for liquid crystal compositions (F. Hoffman-La Roche, Calif. 113:58558, Jpn. Kokai Tokkyo Koho JP 02 25,451 [90.25,451]).

Linking a hydroxyl group to a non-activated carbon atom is a very difficult task if merely "conventional" chemical methods are used therefor. Apart from recently published work using what are termed Gif systems (D. H. R. Barton and W. Chavasiri; Tetrahedron., 1994, 50, 19; D. H. R. Barton and R. D. Doller, Acc. Chem. Res., 1992, 25, 504), there are no purely chemical regioselective methods for hydroxylating non-activated carbon atoms. However, using these Gif systems, hydroxylation could not be performed enantioselectively either. In addition, the yield is so low that these processes are not useful for industrial implementation.

It is not only of importance to position the hydroxyl group regioselectively on a certain carbon atom relative to the carbonyl group. Generally in the course of the hydroxylation a new chiral center is formed. In particular as an intermediate for pharmaceuticals, but also for the agrochemical and cosmetics area, it is of importance that one of the two enantiomers or diastereomers is formed preferentially.

Chemical methods for enantioselective hydroxylation are only available for the α-carbon atom. These are preferably reactions via corresponding enolates, where via suitable complexation using chiral auxiliaries, a certain enantioselectivity is achieved. A disadvantage of using these enantiomer-enriched α-hydroxycarbonyl compounds, is, however, that racemization occurs readily at the α-carbon.

The enzymatic hydroxylation is therefore the only method for solving the set object of the enantioselective hydroxylation of aldehydes and ketones. In this case, especially, numerous examples of hydroxylation of steroides are known, where, as result of the rigid molecular structure, with suitable choice of enzymes or microorganisms, both good regioselectivities and good stereoselectivities were achieved. These reactions are used industrially for the synthesis of pharmaceutically active intermediates.

However, there is no general method for enzymatic hydroxylation of aldehydes and ketones. One reason for this is that, due to the oxidoreductases present in all microorganisms, the carbonyl group itself is reduced, with hydroxylation frequently no longer occurring at all.

With the aid of the concept of the reversible anchor/protecting group, it is possible to carry out a regioselective hydroxylation with chemical yields of up to 70%. This concept is based- on derivatizing the carbonyl group, as result of which it is protected from the biotransformation due to the oxidoreductases. In addition, it is possible to model the chemical and physical properties of the substrate via this protecting group and thus, for example, to decrease the volatility which is interferring for some processes or to introduce a chromophore which is necessary for some chromatographic separations. Suitable anchor/protecting groups are, especially, acetals, aminoacetals, mercaptals or aminals. After carrying out the enzymatic hydroxylation, these protecting/anchor groups are removed again under mild conditions. Hitherto, only non-chiral protecting/anchor groups have been used, as disclosed, for instance, in Chem. Abstr. 125(1), 1996: 10221, which describes the enzymatic hydroxylation of cyclic ketones using the enzyme from Beauveria bassiana ATCC 7159 and the non-chiral N-benzoyl derivative of aminoethanol as protecting group. Although high chemical yields have been achieved, the enantionmeric excess is a maximum of 40% (Biohydroxylation as the Key Step in the Synthesis of Optically Active 3-Substituted Cyclopentanone Derivatives; G. Braunegg, A. de Raadt et al., BIOTRANS '95, University of Warwick, Coventry, Sep. 5–8, 1995, UK).

Owing to the constantly increasing requirement for optically pure hydroxylated oxo compounds, it is desirable to provide processes which are suitable for preparing these compounds in a high optical yield.

Surprisingly, it has now been found that when chiral protecting/anchor groups are used, both the chemical yield and also the enantiomeric excess can be increased considerably.

The invention therefore relates to a process for preparing compounds of the formula

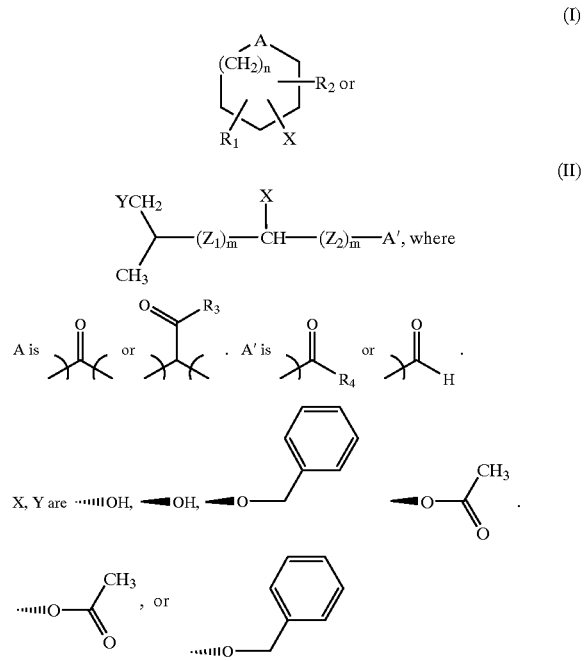

where in the formula II one of the radicals X, Y is hydrogen,
n is one of the integers 0, 1, 2 or 3, where the compounds of the formula I may contain a double bond in the cycle, and
m is one of the numbers 0 or 1,
$Z_1$ and $Z_2$ independently of one another are a $C_1$- to $C_8$-alkylene radical, which may optionally be substituted by $C_1$- to $C_4$-alkyl and/or be unsaturated, R$_1$, R$_2$ independently of one another are hydrogen or unbranched or branched or Cyclic C$_{1-4}$-alkyl or R$_1$ and R$_2$ together with the cycle containing the group A form a bicyclic compound of the structure bicyclo [a, b, c] heptane to decane (a, b, c=0, 1, 2, 3 or 4), which ray optionally be substituted by C$_1$–C$_4$-alkyl and/or be unsaturated, and R$_3$, R$_4$ may be hydrogen or an unbranched, branched or cyclic C$_1$–C$_8$-alkyl, which comprises a compound of the formula

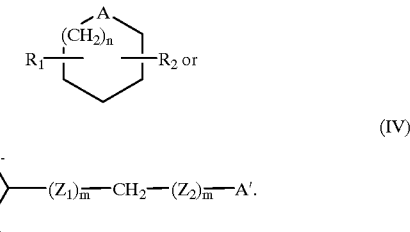

(III)

(IV)

where A, A', R$_1$, R$_2$, R$_3$, R$_4$, Z$_1$, Z$_2$, m and n have the above meaning, being protected with a chiral, aliphatic, cyclic or heterocyclic diol, amino alcohol, acetal, aminoacetal, mercaptol or aminal as anchor/protecting group, the compound protected in this manner being enzymatically regioselectively and stereoselectively hydroxylated, the hydroxyl group being optionally protected with a suitable compound and the anchor/protecting group being removed.

A compound of the formulae (III) or (IV) can be, for example, one of the following

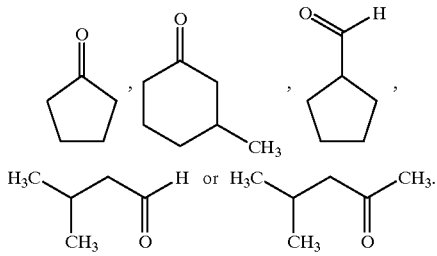

Other suitable compounds of the formula III or IV are, for example bicyclo [2.2.1]heptan-2-one (1R) and (1S)-1,7,7-trimethylbicyclo[2.2.1]heptan-2-one trans-1-decalone 2-decalone (1S) and (1R)-1,3,3-trimethylbicyclo[2.2.1]heptan-2-one bicyclo[3.3.0]octane-3,7-dione bicyclo[3.3.0]octan-3-one bicyclo[3.3.0]oct-7-en-2-one bicyclo[3.3.0]oct-6-en-2-one bicyclo[4.2.0]oct-2-en-7-one bicyclo[3.2.0]hept-2-en-7-one bicyclo[3.2.0]hept-2-en-6-one.

Protecting/anchor groups which can be used are, especially, chiral acetals, aminoacetals, mercaptals or aminals. These may be cyclic or non-cyclic. Preferably, these are 1,2- and 1,3-diols, amino alcohols, dithiols and aminodiols, and also 1,2- and 1,3-diamines. These must have at least one chiral center. These compounds can be aliphatic, alicyclic or heterocyclic. In addition, it is possible that these protecting/anchor groups bear other functional groups, in addition to those groups which are required for the fixing to the substrate molecule.

A preferred anchor/protecting group is a compound of the formulae

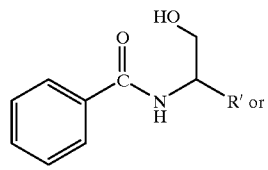

(V)

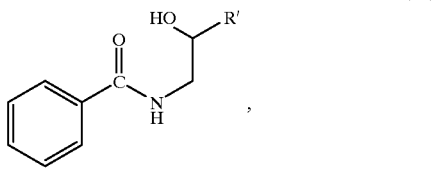

(VI)

where R' is unbranched or branched C$_{1-4}$-alkyl, that is, for example, the N-benzoyl derivatives of (R)-2-amino-1-propanol, (S)-2-amino-1-propanol, (R)-1-amino-2-propanol, (S)-1-amino-2-propanol, (R)-2-amino-1-butanol, (S)-2-amino-1-butanol, (R)-1-amino-2-butanol or (S)-1-amino-2-butanol.

After the enzymatic hydroxylation is carried out, these protecting/anchor groups are then removed again under mild conditions. The cleavage can be carried out using standard chemical methods (T. W. Greene P. G. M. Wuts, "Protective Groups in Organic Synthesis", John Wiley & Sons, Inc 1991), such as by acid-catalyzed hydrolysis, electrolysis or by using metal salts.

Microorganisms which can be used for the hydroxylation are, preferably, the following species. *Aspergillus ochraceus* ATCC 18500, *Bacillus megaterium* CCM 2037, *Bacillus megaterium* DSM 32, *Beauveria bassiana* ATCC 7159, *Calonectria decora* DSM 879, *Chaetomium cochlioides* DSM 831, *Chaetomium globosum* DSM 1962, *Cornyespora cassiicola* DSM 62474, *Corticum sasakii* NRRL 2705, *Cunninghamella blakesleeana* DSM 1906, *Cunninghamella echinulata* DSM 1905, *Cunninghamella elegans* DSM 1908, *Diplodia gossypina* ATCC 10936, *Fusarium solani* DSM 62416, *Mortierella alpina* ATCC 8979, *Mucor plumbeus* CBS 110.16, *Pseudomonas putida* ATCC 29607, *Pellicularia filamentosa* IFO 6298, *Penicillium rastrickii* ATCC 10490, *Polyporus ostreiformis* CBS 36234, Staurophoma species DSM 858 and *Streptomyces griseus* ATCC 13273.

Some of the microorganisms suitable for the process of the invention are known under various synonyms, as listed, for example, in S. C. Long, J. M. Birminghan, G. Ma, "ATCC Names of Industrial Fungi", American Type Culture Collection, USA, 1994.

However, it is possible in an identical manner to find further microorganisms via screening or to isolate further microorganisms from natural sources, such as soil samples, waste or wastewater, via enrichment and selection methods.

The enzyme preparations used according to the invention are not restricted with respect to purity and the like and can be used, for example, as impure enzyme solution.

They can, however, also consist of optionally immobilized cells having the desired activity or of a homogenate of cells having the desired activity.

The invention is not restricted here in any manner by the form in which the enzyme is used. In the context of the invention it is further possible to use enzymes which are derived from a mutant, or genetically modified microorganisms.

EXAMPLES

Example 1

(R)-3-Benzyloxycyclopentanone
(3R)-4-Benzoyl-3-methyl-1-oxa-4-azaspiro[4.4]nonane (Saaverda, J. Org Chem., 1985, 50, 2379)

Cyclopentanone (1.80 g, 0.021 mol) and (R)-2-amino-1-propanol (1.07 g, 0.014 mol) were added to a suspension of $K_2CO_3$ (3.94 g, 0.029 mol) in $CH_2Cl_2$ (10 ml) and stirred for 48 hours at room temperature. Benzoyl chloride (2.01 g, 0.014 mol) was added to the reaction mixture and it was stirred for a further 48 hours. The mixture was filtered and the filtrate was washed successively with 100 ml each time of 5% aq. HCl, sat. aq. $Na_2CO_3$ and $H_2O$, The organic phase was dried over $Na_2SO_4$ and concentrated on a rotary evaporator.

(3R)-4-Benzoyl-3-methyl-1-oxa-4-azaspiro[4.4]nonane was obtained as a light yellow solid after column chromatography and recrystallization from ethyl acetate/petroleum ether (yield 75%).

ee: 98% (HPLC, CHIRALCEL OD-H, n-heptane: IPA; 7:3 p=38 bar; Flow rate =0.5 ml/min); m.p.: 65.5–67.5° C.; $[\alpha]_D^{20}$=−79.8° (c 2.1, $CH_2Cl_2$); $^1$H NMR: δ 0.96 (d, $J_{3,Me}$=6.5 Hz, 3H, Me), 1.64–1.98, 2.37–2.71 (2×m, 6H & 2H, H6, 7, 8, 9), 3.60 (m, 1H, H2), 4.00 (m, 2H, H2.3), 7.40 (s, 5H, benzoyl). $^{13}$C NMR: δ 20.1 (Me), 24.7, 24.8 (C7.8), 35.0, 36.5 (C6.9), 54.1 (C3), 70.0 (C2), 105.0 (C5), 126.2, 128.4, 128.5, 129.4, 138.2, 168.1 (benzoyl).

(3R,5S,7R)-4-Benzoyl-3-methyl-1-oxa-4-azaspiro[4.4]nonan-7-ol

The fungus *Beauveria bassiana* ATCC 7159 was grown for 1 week on medium E (15 g/l of agar, 10 g/l of glucose, 5 g/l of peptone, 5 g/l of malt extract, 2 g/l of yeast extract, 2 g/l of $KH2PO_4$) in Petri dishes. 1 cm$^2$ was used of this in order to inoculate the preliminary culture (70 ml, medium E, 30° C., 120 rpm). After 72 hours, the main culture was inoculated in the fermenter with 10% of the volume of preliminary culture (fermenter conditions: 1.6 l working volume; pH=6.6–7;T=28° C.; aeration: 1.6 L (S.T.P.)/min; 400 rpm; medium E; 0.25 ml PPG 2000 as antifoamer)

After 24 hours of main culture growth, 0.16 g of (3R)-4-benzoyl-3-methyl-1-oxa-4-azaspiro[4.4]nonane, dissolved in EtOH (solution, 20% wiv), was added. The main portion of substrate (0.64 g) was added after a further 12 hours.

The fermentation was terminated as soon as substrate was no longer detectable when following the course of the hydroxylation by GC (HP 5890, series II, column HP5, 25 m, FID) and TLC (Merck 5642.001). The culture was extracted twice using ethyl acetate, the organic phase was dried over $Na_2SO_4$, filtered and the filtrate concentrated on a rotary evaporator. By means of column chromatography (Merck silica gel 60, 70–230 mean particle size), the hydroxylated product, (3R,5S,7R)-4-benzoyl-3-methyl-1-oxa-4-azaspiro[4.4]-nonan-7-ol, was isolated (0.72 g, 84%). The diastereomer excess was determined firstly at 11:1 (HPLC, CHIRALCEL OD-H n-heptane: IPA; 7.3; P=37 bar; flow rate=0.50 ml/min—prior to column chromatography), secondly at 20:1 (HPLC, after column chromatography).

$[\alpha]_D^{20}$=−79.60 (c 1.5, $CH_2Cl_2$); m.p.: 106–108° C.; $^1$H NMR: δ 0.93 (d $J_{3,Me}$=5.7 Hz, 3H, Me); 1.73–2.41 (m, 4H, H6, 8, 9, 9), 2.57–2.69 (m, 2H, H8, OH), 2.75, 2.94 (2×dd; $J_{6,7}$=5.7 Hz, $J_{6,6'}$=14.0 Hz, ratio: 20:1, H6), 3.63 (dd, $J_{2,3}$=5.1 Hz, $J_{2,2}$=11.3 Hz, 1H, H2), 3.98 (m, 2H, H2, H3), 4.42 (br s, 1H, H7), 7.37 (s, 5H, benzoyl); $^{13}$C NMR: δ 20.1 (Me), 34.7, 34.8 (C8, 9), 43.2 (C6), 54.0 (C3), 70.3 (C2), 72.7 (C7), 104.0 (C5), 126.2, 128.6, 129.6, 137.7, 168.2 (benzoyl).

(3R, 5S, 7R)-4-Benzoyl-7-benzyloxy-3-methyl-1-oxa-4-azaspiro [4.4]nonane

Before the protecting group was removed, (3R, 5S, 7R)-4-benzoyl-3-methyl-1-oxa-4-azaspiro[4.4]nonan-7-ol was derivatized (NaH, benzyl bromide, THF, DMF, room temperature), After column chromatography, (3R, 5S, 7R)-4-benzoyl-7-benzyloxy-3-methyl-1-oxa-4-azaspiro[4.4] nonane was obtained as fine needles in a yield of 85% de: 89% (NMR); $[\alpha]_D^{20}$: −75.2° (c 3.0, $CH_2Cl_2$); m.p.: 85–86° C. ($CH_2Cl_2$/Pet. ether); 1H NMR: δ (minor isomer in bold) 0.95 (d, $J_{3,Me}$=6.6 Hz, 3H, Me), 1.83–2.67 (m, 5H, H6, 8, 9), 2.77, 2.96 (2×dd; $J_{6,7}$=6.7 Hz, $J_{6,6}$=14.4 Hz, 1H, ratio: 18:1, H6), 3.64 (m, 1H, H2), 4.03 (m, 2H, H2, H3), 4.33 (br s, 1H, H7), 4.54 (s, 2H, C$\underline{H}_2$Ph), 7.34 (m, 10H, CO Ph, CH$_2$P$\underline{h}$). $^{13}$C NMR: δ 20.1 (Me), 31.7, 35.3 (C8, 9), 41.9 (C6), 54.0 (C3), 70.4 (C2), 70.9 ($\underline{C}H_2$Ph), 79.2 (C7), 103.3 (C5), 126.3, 127.5, 127.7, 128.4, 128.4, 128.6, 129.7, 137.9, 138.9 (COP$\underline{h}$, CH$_2$P$\underline{h}$), 168.2 ($\underline{C}$OPh).

(R)-3-Benzyloxycyclopentanone (3R, 5S, 7R)-4-Benzoyl-7-benzyloxy-3-methyl-1-oxa-4-azaspiro[4.4]nonane (250 mg, 0.7 mmol) were dissolved in 5 ml of $CH_3CN$. IR 120[H$^+$] (washed 2× with ethanol and 1× with $H_2O$) was added to a pH of 5–6, The mixture was stirred at room temperature until starting material was no longer detectable. The reaction mixture was filtered and the filtrate was concentrated on a rotary evaporator. After column chromatography, (R)-3-benzyloxycyclopentanone (81 mg, 0.4 mmol) was obtained.

ee: 84% (chiral GC; Macherey—Nagel, Lipodex E); Yield: 61%; $[\alpha]_D^{20}$: =−43.0° (c 1.0, $CH_2Cl_2$); m.p.: sirup; $^1$H NMR and $^{13}$C NMR are identical with the literature values (T. H. Eberlein, F. G. West, R. W. Tester, J. Org. Chem., 1992, 57, 3479–3482);

Examples 2 to 7 were carried out in the manner described in Example 1, but using other aldehydes/ketones and anchor/protecting groups.

Example 2

(R)-3-Benzyloxycyclopentanone

Anchor/protecting group: (R)-2-amino-1-butanol
(3R) -4-Benzoyl-3-ethyl-1-oxa-4-azaspiro[4.4]nonane ee: 90% HPLC (CHIRALCEL OD-H, n-heptane: IPA; 7:3; P=40 bar, flow rate=0.50 ml/min). Yield: 57%; $[\alpha]_D^{20}$: =−59.4° (c 3.9, $CH_2Cl_2$); m.p. waxy; $^1$H NMR: δ 0.61 (t, J=7.3 hz, 3H, CH$_2$C$\underline{H}_3$), 1.31 (m, 2H, C$\underline{H}_2$CH$_3$), 1.58–2.03, 2.31–2.72 (2×m, 6H & 2H, H6, 7, 8, 9), 3.68–3.99 (m, 3H, H2.3), 7.37 (s, 5H, benzoyl). $^{13}$C NMR: δ 9.9 (CH$_2$$\underline{C}$H$_3$), 24.8, 24.8, 26.4 (C7, 8, $\underline{C}$H$_2$CH$_3$), 35.0, 36.3 (C6, 9), 59.6 (C3), 67.3 (C2), 104.9 (C5), 126.3, 128.4, 129.4, 138.2, 168.1 (benzoyl).

(3R,7R)-4-Benzoyl-3-ethyl-1-oxa-4-azaspiro[4.4]nonan-7-ol de: 7:1 (75%) (after column chromatography); Yield: 82%. m.p.: sirup. $^1$H NMR: δ (minor isomer in bold) 0.60 (t, J=7.4 Hz, 3H, CH$_2$C$\underline{H}_3$), 1.11–1.43 (br, m, 2H, C$\underline{H}_2$CH$_3$), 1.69–2.62 (m, 6H, H6, 8, 9, OH), 2.69, 2.90 (2×dd, $J_{6,7}$=5.7 Hz, $J_{6,6}$=13.7 Hz, 1H, ratio: 7:1, H6), 3.70–3.99 (m, 3H, H2.3), 4.41 (br, s, 1H, H7), 7.36 (s, 5H, benzoyl). $^{13}$C NMR: δ (minor isomer in bold) 9.9 (CH$_2$$\underline{C}$H$_3$), 26.3, 26.4 ( CH₂CH₃), 33.6, 34.5, 43.1, 44.7 (C6, 8, 9), 59.4 (C3), 67.5, 67.6, (C2), 72.7, 72.8 (C7), 103.9 (C5), 126.2, 128.4, 128.4, 128.5, 129.7, 137.7, 168.3 (benzoyl).

(3R,7R)-4-Benzoyl-7-benzyloxy-3-ethyl-1-oxa-4-azaspiro[4.4]nonane de: 7:1 (75%) (NMR); Yield: 75%; m.p.: sirup. $^1$H NMR: δ (minor isomer in bold) 0.64 (t, J=7.4 Hz, 3H, CH₂C$\underline{H}$₃), 1.20–1.43 (br, m, 2H, C$\underline{H}$₂CH₃), 1.84–2.09 & 2.20–2.65 (2×m, 5H, H6, 8, 9), 2.76, $\overline{2.98}$ (2×dd, $J_{6,7}$=6.9 Hz, $J_{6,6}$=14.1 Hz, 1H, ratio: 7:1, H6), 3.76–4.03 (m, 3H, H2,3), 4.33 (br, s, 1H, H7), 4.55 (m, 2H, CH₂Ph), 7.22–7.47 (m, 10H, CH₂P$\underline{h}$, COP$\underline{h}$). $^{13}$C NMR: δ ($\overline{\text{minor}}$ isomer in bold) 9.9 (CH₂$\underline{C}$H₃), 26.5, 31.8, 34.0, 35.3 (C8, 9, $\underline{C}$H₂CH₃), 42.1 43.0, (C6), 59.6, 59.7 (C3), 67.8, 67.9 (C2), 71.0, 71.3, (C$\underline{H}$₂Ph), 79.3, 79.6, (C7), 103.5 (C5), 126.5, 127.6, 127.8, 128.5, 128.7, 129.7, 129.8, 138.2, 139.2 (CH₂P$\underline{h}$, COP$\underline{h}$), 168.4 ($\underline{C}$OPh).

(R)-3-Benzyloxycyclopentanone ee: 76% (chiral GC; Macherey—Nagel, Lipodex E); Yield: 77%; m.p.: sirup. $^1$H NMR and $^{13}$C NMR are identical with the literature values (T. H. Eberlein, F. G. West, R. W. Tester, J. Org. Chem., 1992, 57, 3479–3482).

Example 3

(R)-3-Benzyloxycyclopentanone

Anchor/protecting group: (S)-1-amino-2-propanol (2S)-4-Benzoyl-2-methyl-1-oxa-4-azaspiro[4.4]nonane ee: 99%; Yield: 50%; $[\alpha]_D^{20}$=+120.6 (c 2.2, CH₂Cl₂); m.p.: sirup. $^1$H NMR: δ 1.27 (d, $J_{2,Me}$=5.9 Hz, 3H, Me); 1.59–2.03 & 2.35–2.75 (2×m, 6H, 2H, H6, 7, 8, 9); 3.19 (dd, $J_{2,3}$#=$J_{3,3\#}$=9.5 Hz, 1H, H3#); 3.45 (dd, $J_{2,3}$=5.2 Hz, 1H, H3), 4.04 (m, 1H, H2); 7.33–7.51 (m, 5H, benzoyl). $^{13}$C NMR: δ 17.5 (Me), 24.5, 25.2 (C7, 8), 35.2, 36.1 (C6, 9), 55.6 (C3), 70.8 (C2), 105.0 (C5), 126.6, 128.4, 129.8, 137.9, 167.4 (benzoyl).

(2S,7R)-4-Benzoyl-2-methyl-1-oxa-4-azaspiro[4.4]nonan-7-ol de: 11:1 (HPLC, CHIRALCEL OD-H—n-heptane: IPA; 7:3; P=38 bar; flow rate=0.50 ml/min—after chromatography) Yield: 77%; $[\alpha]_D^{20}$=+87.8° (c 1.6 CH₂Cl₂); m.p.: sirup; $^1$H NMR: δ (minor isomer in bold) 1.26 (d, $J_{2,Me}$=6.0 Hz, 3H, Me), 1.69–2.37 & 2.53–2.69 (m, 5H, H6, 8, 9), 2.76, 2.93 (2×dd; $J_{6\#7}$=5.9 Hz, $J_{6,6\#}$=13.9 Hz, 1H, ratio: 11:1, H6) 3.19 (dd, $J_{2,3\#}$=$J_{3,3\#}$=9.6 Hz, 1H, H3#), 3.45 (dd, $J_{2,3}$=5.3 Hz, 1H, H3), 4.06 (m, 1H, H2), 4.46 (m, 1H, H7), 5.15 (br s, 1H, OH), 7.42 (m, 5H, benzoyl). $^{13}$C NMR: δ 17.4 (Me), 34.2, 43.3 (C6, 8, 9), 55.3 (C3), 71.4 (C2), 73.3 (C7), 104.0 (C5), 126.6, 128.4, 130.1, 137.3, 167.7 (benzoyl).

(2S,7R)-4-Benzoyl-7-benzyloxy-2-methyl-1-oxa-4-azaspiro[4.4]nonane de: 18:1 (NMR); Yield: 43%; $[\alpha]_D^{20}$=+62.70 (c 2.7, CH₂Cl₂); m.p.: sirup. $^1$H NMR: δ (minor isomer in bold) 1.31 (d, $J_{2,Me}$=5.9 Hz, 3H, Me), 1.84–2.39 & 2.52–2.73 (m, 5H, H6, 8, 9), 2.81, 2.96 (2×dd; $J_{6\#7}$=7.0 Hz, $J_{6,6\#}$=13.8 Hz, 1H, ratio: 18:1, H6) 3.22 (dd, $J_{2,3\#}$=$J_{3,3\#}$=9.6 Hz, 1H, H3#), 3.47 (dd, $J_{2,3}$=5.2 Hz, 1H, H3), 4.06 (m, 1H, H2), 4.38 (m, 1H, H7), 4.55 (s, 2H, C$\underline{H}$₂Ph), 7.21–7.57 (m, 10H, CH₂P$\underline{h}$, COP$\underline{h}$). $^{13}$C NMR: δ 17.6 (Me), 31.5, 34.9 (C8, 9), 42.3 (C6), 55.5 (C3), 70.9, 71.1 (C2, $\underline{C}$H₂Ph), 79.8 (C7), 103.2 (C5), 126.8, 127.0, 127.5, 127.8, 128.4, 128.4, 128.8, 130.1, 137.6, 139.0 (CH₂P$\underline{h}$, COP$\underline{h}$), 167.6 ($\underline{C}$OPh).

(R)-3-Benzyloxycyclopentanone ee: 91% (chiral GC); Yield: 82%; m.p.: sirup. $^1$H NMR and $^{13}$C NMR are identical with the literature values (T. H. Eberlein, F. G. West, R. W. Tester, J. Org. Chem., 1992, 57, 3479–3482).

Example 4

(3S,4S)-4-Hydroxy-3-methylcyclohexanone

Anchor/protecting group: (R)-2-amino-1-propanol (3R,5R/S,7R)-4-Benzoyl-3,7-dimethyl-1-oxa-4-azaspiro[4.4]decane de: 5R:5S; 4.4:1 (HPLC, CHIRALCEL OD-H—n-heptane: IPA; 4:1; P=34 bar; flow rate=0.5 ml/min).

Purity of the starting materials (Aldrich):
(R)-(+)-3-methylcyclohexanone (98% ee)
(R)-(−)-2-amino-1-propanol (98% ee)

Yield: 76%; $[\alpha]_D^{20}$=−45.4° (c 1.4, CH₂Cl₂); m.p.: 62–72° C.; $^1$H NMR: δ 0.82–1.16 (m, 6H, 2×Me), 1.43–2.87 (m, 9H, H6, 7, 8, 9, 10), 3.60 (m, 1H, H2), 4.01 (m, 2H, H2, 3), 7.38 (s, 5H, benzoyl). $^{13}$C NMR: δ (minor isomer in bold) 19.9, 20.7, 20.8, 22.4 (Me), 22.8 (C9), 28.2, 29.9 (C7), 30.1, 30.2 (C8), 33.3, 34.8 (C10), 43.4 (C6), 54.2, 54.5 (C3), 69.3, 69.4 (C2), 97.4 (C5), 126.1, 128.5, 129.2, 138.6, 168.4 (benzoyl).

(3R,5R,7S,8S)-4-Benzoyl-3,7-dimethyl-1-oxa-4-azaspiro[4.4]decan-8-ol de: 95% HPLC (CHIRALCEL OD-H, n-heptane: IPA; 7:3; P=40 bar; flow rate=0.5 ml/min); Yield: 40%; $[\alpha]_D^{20}$=−33.20 (c 0.5, CH₂Cl₂); m.p.: 215–218° C.; $^1$H NMR: δ 0.98 & 1.03 (2×d, J=6.7 & 6.4 Hz, 6H, 2×Me), 1.54–1.95 & 2.63 (m & br m, 6H & 2H, H6, 7, 9, 10, OH), 3.31 (ddd, $J_{8,9ax}$=$J_{8,7ax}$=10.8 Hz, $J_{8,9eq}$=4.2 Hz, 1H, H8), 3.63 (m, 1H, H2), 4.02 (m, 2H, H2, 3), 7.37 (s, 5H, benzoyl). $^{13}$C NMR: δ 18.2, 20.6 (Me), 29.2 (C9), 31.8 (C10), 36.7 (C7), 41.1 (C6), 54.6 (C3), 69.4 (C2), 74.8 (C8), 96.3 (C5), 126.1, 128.5, 129.3, 138.3, 168.5 (benzoyl).

(3S,4S)-4-Hydroxy-3-methylcyclohexanone de: 1 diastereomer; Yield: 81%; $[\alpha]_D^{20}$=+22.0° (c 0.6, CH₂Cl₂); m.p.: sirup; $^1$H MMR: δ 1.05 (d, J=6.1 Hz, 3H, Me), 1.68–2.59 (m, 8H, H2, 3, 5, 6, OH), 3.69 (ddd, $J_{4,5ax}$=$J_{4,3ax}$=8.1 Hz, $J_{4,5eq}$=3.7 Hz, 1H, H4). $^{13}$C NNR: δ 18.6 (Me), 32.4, 38.4, 39.5 (C2, 5, 6), 45.7 (C3), 72.8 (C4), 210.5 (C1).

Example 5

3-Acetoxycylopentanecarboxaldehyde

Anchor/protecting group: (R)-2-amino-1-propanol (4R)-N-Benzoyl-2-cyclopentyl-4-methyloxazolidine de: 1 diastereomer (NMR); Yield: 28%; $[\alpha]_D^{20}$=+107.5° (c 1.1, CH₂Cl₂); m.p.: light-yellow oil. $^1$H NMR: δ 1.13–1.85 (br m, 11H, H2', 3', 4', 5', Me), 2.29 (br s, 1H, H1'), 3.54–4.03 (m, 3H, H4, 5), 5.46 (d, $J_{2,1'}$=5.7 Hz, 1H, H2), 7.38 (m, 5H, benzoyl). $^{13}$C NMR: δ 20.9 (Me), 25.3, 27.3, 28.4 (C2', 3', 4', 5'), 44.1 (C1'), 54.3 (C4), 71.9 (C5), 92.5 (C2), 126.6, 128.5, 130.0, 137.4, 170.5 (benzoyl).

(4R)-N-Benzoyl-2-(3'-hydroxycyclopentyl)-4-methyloxazolidine

Yield: 30%; $[\alpha]_D^{20}$=+104.9° (c 3.9, CH₂Cl₂); m.p.: 83–85° C.; $^1$H NMR: δ (minor isomer in bold) 1.14–2.22 (4×br m, 10H, H2', 4', 5', Me, OH), 2.64 (br s, 1H, H1'), 3.64–3.99 (m, 3H, H4, 5), 4.21, 4.33 (2×br s, 1H, ratio: 1:3.5, H3'), 5.42 (m, 1H, H2), 7.43 (m, 5H, benzoyl). $^{13}$C NMR: δ 20.9, 21.1 (Me), 25.3, 25.4, 26.0, (C5'), 35.0, 35.1, 35.7, 35.7, 37.1, 38.2, 40.1 (C2', 4'), 41.5, 41.9 (C1'), 54.3, 54.5 (C4), 71.6, 71.9, 72.0 (C5), 73.1, 73.3, 73.3, 73.4 (C3'), 92.2, 92.4, 92.5 (C2), 126.4, 126.5, 126.6, 126.9, 127.0, 127.1, 127.1, 128.4, 128.5, 128.9, 130.1, 137.1, 137.2, 171.2 (benzoyl).

(4R)-N-Benzoyl-2-(3'-acetoxycyclopentyl)-4-methyloxazolidine

Yield: 83%; m.p.: sirup. $^1$H NMR: δ (minor isomer in bold) 1.29 (d, $J_{4,Me}$=6.4 Hz, 3H, Me), 1.54–2.26 (3×m, s, 9H, H2', 4', 5', COC$\underline{H}_3$), 2.40, 2.66 (2×br s, 1H, ratio: 1:3.5, H1'), 3.65–3.98 (m, 3H, H4, 5), 5.03, 5.24 (2×br s, 1H, H3'), 5.42, 5.49 (2×d, $J_{2,1}$=5.1 & 5.7, ratio: 3:1, 1H, H2), 7.42 (m, 5H, benzoyl). $^{13}$C NMR: δ (minor isomer in bold) 21.0, 21.4 (2×Me), 24.9, 26.1, 26.1 (C5'), 32.1, 32.2, 33.7, 35.2 (C2', 4'), 41.2, 41.6, 42.5 (C1'), 54.4 (C4), 72.0 (C5), 75.9, 76.7 (C3'), 91.8, 92.0, 92.0 (C2), 126.6, 128.5, 130.1, 137.2, 170.8 (benzoyl).

Example 6

(R)-3-Benzyloxycyclopentanone

Anchor/protecting group: (R)-1-amino-2-propanol (2R)-4-Benzoyl-2-methyl-1-oxa-4-azaspiro[4 4]nonane ee: 98%; Yield: 39%; [α]$_D^{20}$=−123.50 (c 2.3, CH$_2$Cl$_2$); m.p.: sirup; $^1$H NMR: δ 1.27 (d, $J_{2,Me}$=6.1 Hz, 3H, Me); 1.56–2.05 & 2.36–2.75 (2×m, 6H, 2H, H6, 7, 8, 9); 3.20 (dd, $J_{2,3\#}$=$J_{3,3\#}$=9.5 Hz, 1H, H3$^\#$); 3.45 (dd, $J_{2,3}$=5.1 Hz, 1H, H3), 4.03 (m, 1H, H2); 7.33–7.51 (m, 5H, benzoyl). $^{13}$C NMR: δ 17.5 (Me), 24.5, 25.2 (C7, 8), 35.2, 36.1 (C6, 9), 55.6 (C3), 70.8 (C2), 105.0 (C5), 126.6, 128.4, 129.8, 137.9, 167.4 (benzoyl).

(2R,7R)-4-Benzoyl-2-methyl-1-oxa-4-azaspiro[4.4]nonan-7-ol de: 1:6 (71%, NMR, after chromatography); Yield: 28%; [α]$_D^{20}$=not determined owing to the low de; m.p.: sirup; $^1$H NMR: δ (minor isomer in bold) 1.23 (d, $J_{2,Me}$=5.9 Hz, 3H, Me), 1.68–2.56 (m, 5H, H6, 8, 9), 2.73, 2.90 (2×dd; $J_{6\#,7}$=6.3 Hz, $J_{6,6\#}$=14.0 Hz, 1H, ratio: 6:1, H6) 3.17 (dd, $J_{2,3\#}$=$J_{3,3\#}$=9.7 Hz, 1H, H3$^\#$), 3.43 (dd, $J_{2,3}$=5.3 Hz, 1H, H3), 4.03 (m, 1H, H2), 4.46 (m, 1H, H7), 5.04 (br s, 1H, OH), 7.39 (m, 5H, benzoyl). $^{13}$C NMR: δ (minor isomer in bold) 17.4 (Me), 33.8, 34.6, 43.2, 44.5 (C6, 8, 9), 55.3 (C3), 71.4 (C2), 72.2, 73.3 (C7), 103.5, 104.0 (C5), 126.6, 128.4, 130.2, 137.2, 167.8 (benzoyl).

(2R,7R)-4-Benzoyl-7-benzyloxy-2-methyl-1-oxa-4-azaspiro[4.4]nonane de: 6:1 (71%, NMR); Yield: 56%; [α]$_D^{20}$=not determined owing to the low de; m.p.: sirup; $^1$H NMR: δ (minor isomer in bold) 1.31 (d, $J_{2,Me}$=6.0 Hz, 3H, Me), 1.77–2.70 (m 5H, H6, 8, 9), 2.81, 2.94 (2×dd; $J_{6\#,7}$=7.7 Hz, $J_{6,6\#}$=14.1 Hz, 1H, ratio: 6:1, H6) 3.22 (dd, $J_{2,3\#}$=$J_{3,3\#}$=9.5 Hz, 1H, H3$^\#$), 3.48 (dd, $J_{2,3}$=5.2 Hz, 1H, H3), 4.08 (m, 1H, H2), 4.40 (m, 1H, H7), 4.54 (s, 2H, C$\underline{H}_2$Ph), 7.21–7.57 (m, 10H, CH$_2$$\underline{Ph}$, CO $\underline{Ph}$). $^{13}$C NMR: δ 17.5 (Me), 32.1, 33.9 (C8, 9), 42.8 (C6), 55.3 (C3), 71.3, 71.3 (C2, $\underline{C}H_2$Ph), 78.8 (C7), 102.7 (C5), 126.7, 126.7, 127.4, 127.8, 128.4, 128.4, 130.1, 137.5, 139.0 (CH$_2$$\underline{Ph}$, CO$\underline{Ph}$), 167.5 ($\underline{C}$OPh).

(R)-3-Benzyloxycyclopentanone ee: 71% (chiral GC; Macherey—Nagel, Lipodex E); Yield: 77%; [α]$_D^{20}$=−; m.p.: sirup; $^1$H NMR and $^{13}$C NMR are identical with the literature values (T. H. Eberlein, F. G. West, R. W. Tester, J. Org. Chem., 1992, 57, 3479–3482)

Example 7

(R)-3-Benzyloxycylopentanone

Anchor/protecting group: (S)-2-amino-1-propanol (3S)-4-Benzoyl-3-methyl-1-oxa-4-azaspiro[4.4]nonane ee: 98%; Yield: 89%; [α]$_D^{20}$=+76.40 (c 2.7, CH$_2$Cl$_2$); m.p.: 65.5–67.5° C. (EtOAc/Pet. ether) pale-yellow solid. $^1$H NMR: δ 0.93 (m, 3H, Me), 1.57–2.03, 2.32–2.71 (2×m, 6H & 2H, H6, 7, 8, 9), 3.57 (m, 1H, H2), 3.98 (m, 2H, H2, 3), 7.38 (s, 5H, benzoyl). $^{13}$C NMR: δ 20.1 (Me), 24.7, 24.8 (C7, 8), 35.0, 36.5 (C6, 9), 54.1 (C3), 70.0 (C2), 105.0 (C5), 126.2, 128.4, 128.5, 129.4, 138.2, 168.0 (benzoyl).

(3S,7R)-4-Benzoyl-3-methyl-1-oxa-4-azaspiro[4.4]nonan-7-ol de: 1:3 (50%), NMR, after chromatography; Yield: 35%. [α]$_D^{20}$=not determined because of the low de. m.p.: sirup. $^1$H NMR: δ (minor isomer in bold) 0.94 (m, 3H, Me); 1.74–2.70 (m, 6H, H6, 8, 9, OH), 2.76, 3.01 (2×dd; $J_{6,7}$=5.9 Hz, $J_{6,6}$=14.0 Hz, 1H, ratio: 3:1, H6), 3.63 (m, 1H, H2), 4.02 (m, 2H, H2, H3), 4.47 (br s, 1H, H7), 7.38 (s, 5H, benzoyl). $^{13}$C NMR: δ (minor isomer in bold) 20.1, 20.3 (Me), 33.8, 34.6, 34.7, 34.9 (C8, 9), 43.4, 45.0 (C6), 54.2 (C3), 70.5 (C2), 73.0 (C7), 104.0, 104.2, (C5), 126.4, 128.7, 129.8, 138.1, 168.5 (benzoyl).

(3S,7R)-4-Benzoyl-7-benzyloxy-3-methyl-1-oxa-4-azaspiro[4.4]nonane de: 1:2 (33%, NMR); Yield: 78%; [α]$_D^{20}$=not determined because of the low de. m.p.: sirup; $^1$H NMR: δ (minor isomer in bold) 0.96 (m, 3H, Me); 1.79–2.66 (m, 5H, H6, 8, 9), 2.78, 2.96 (2×dd; $J_{6,7}$=7.3 Hz, $J_{6,6}$=14.4 Hz, 1H, ratio: 2:1, H6), 3.56 (m, 1H, H2), 4.03 (m, 2H, H2, H3), 4.33 (br s, 1H, H7), 4.54 (m, 1H, C$\underline{H}_2$Ph), 7.34 (m, 10H, benzoyl, benzyl). $^{13}$C NMR: δ (minor isomer in bold) 20.1 (Me), 31.5, 31.7, 33.9, 34.1 (C8, 9), 41.9, 43.0 (C6), 54.0, 54.1 (C3), 70.3, 70.4 (C2), 70.9, 71.1 ($\underline{C}H_2$Ph), 79.1, 79.2 (C7), 103.0 (C5), 126.2, 126.2, 127.4, 127.8, 128.3, 128.5, 129.6, 129.7, 138.0, 138.8, 168.3 (benzoyl, benzyl).

(R)-3-Benzyloxycyclopentanone ee: 29% (chiral GC; Macherey - Nagel, Lipodex E); Yield: 74%; [α]$_D^{20}$=−; m.p.: sirup; $^1$H NMR and $^{13}$C NMR are identical with the literature values (T. H. Eberlein, F. G. West, R. W. Tester, J. Org. Chem., 1992, 57, 3479–3482).

What is claimed is:
1. Process for preparing compounds of the formula

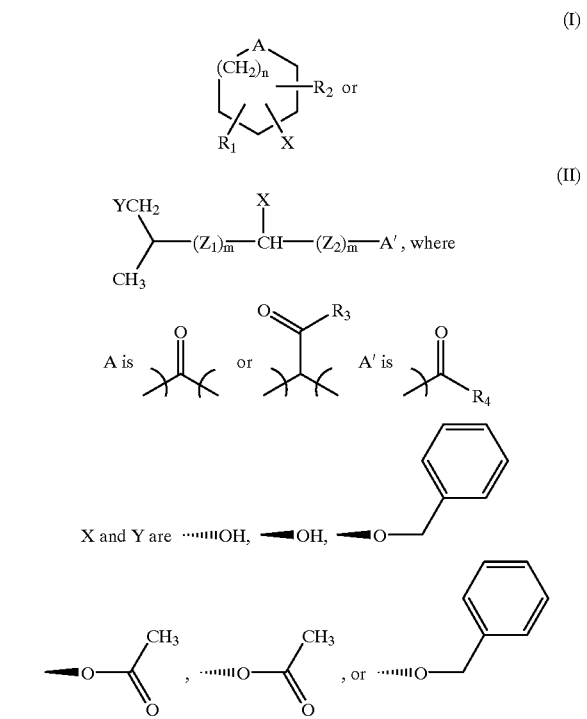

where in the formula II one of the radicals X, Y is hydrogen,
n is one of the integers 0, 1, 2 or 3, where the compounds of the formula I may contain a double bond in the ring, and
m is one of the numbers 0 or 1,
$Z_1$ and $Z_2$ independently of one another are a $C_1$- to $C_8$-alkylene radical, which may optionally be substituted by $C_1$- to $C_4$-alkyl and/or be an alkenylene radical, $R_1$, $R_2$ independently of one another are hydrogen or unbranched or branched or cyclic $C_{1-4}$-alkyl or $R_1$ and $R_2$ together with the ring containing the group A form a bicyclic compound of the structure bicycloheptane to decane (a, b, c=0, 1, 2, 3 or 4), which may optionally be substituted by $C_1$–$C_4$-alkyl and/or alkene, and $R_3$, $R_4$ may be hydrogen or an unbranched, branched or cyclic $C_1$–$C_8$-alkyl, which comprises reacting a compound of the formula

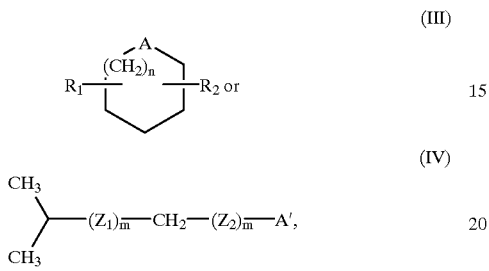

where A, A', $R_1$, $R_2$, $R_3$, $R_4$, $Z_1$, $Z_2$, m and n have the above meaning, being protected with a chiral, aliphatic, cyclic or heterocyclic diol, amino alcohol, acetyl, aminoacetal, mercaptol or aminal as anchor/protecting group, the compound protected in this manner being enzymatically regioselectively and stereoselectively hydroxylated, the hydroxyl group being optionally protected with a protecting group and the anchor/protecting group being removed.

2. The process as claimed in claim 1, wherein the compound of the formula (III) or (IV) is one of the following compounds:

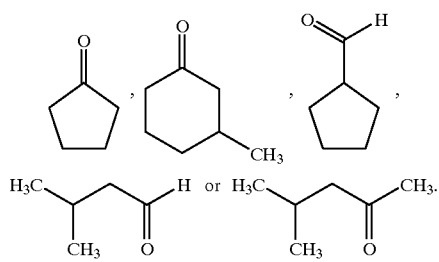

or bicyclo[2.2.1]heptan-2-one, (1R) and (1S)-1,7,7-trimethylbicyclo[2.2.1]heptan-2-one, trans-1-decalone, 2-decalone, (1S) and (1R)-1,3,3-trimethylbicyclo[2.2.1]heptan-2-one, bicyclo[3.3.0]octane-3,7-dione, bicyclo[3.3.0]octan-3-one, bicyclo[3.3.0]oct-7-en-2-one, bicyclo[3.3.0]oct-6-en-2-one, bicyclo[4.2.0]oct-2-en-7-one, bicyclo[3.2.0]hept-2-en-7-one, bicyclo[3.2.0]hept-2-en-6-one.

3. The process as claimed in claim 1, wherein the compound of the formula (III) or (IV) used is one of the following compounds:

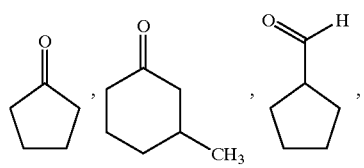

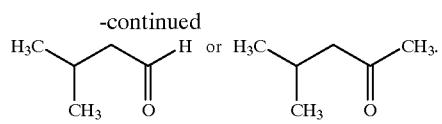

4. The process as claimed in claim 1, wherein the anchor/protecting group used is a compound of the formula

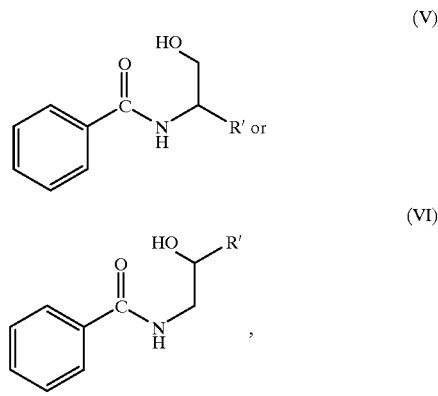

where R' is unbranched or branched $C_{1-4}$-alkyl.

5. The process as claimed in claim 1, wherein the anchor/protecting group used is the N-benzoyl derivative of one of the following compounds:

(R)-2-amino-1-propanol, (S)-2-amino-1-propanol, (R)-1-amino-2-propanol, (S)-1-amino-2-propanol, (R)-2-amino-1-butanol, (S)-2-amino-1-butanol, (R)-1-amino-2-butanol or (S)-1-amino-2-butanol.

6. The process as claimed in claim 1 wherein the enzymatic-hydroxylation is carried out using one of the following microorganisms:

Aspergillus ochraceus ATCC 18500, Bacillus megaterium CCM 2037, Bacillus megaterium DSM 32, Beauveria bassiana ATCC 7159, Calonectria decora DSM 879, Chaetomium cochlioides DSM 831, Chaetomium globosum DSM 1962, Cornyespora cassiicola DSM 62474, Corticum sasakii NRRL 2705, Cunninghamella blakesleeana DSM 1906, Cunninghamella echinulata DSM 1905, Cunninghamella elegans DSM 1908, Diplodia gossypina ATCC 10936, Fusarium solani DSM 62416, Mortierella alpina ATCC 8979, Mucor plumbeus CBS 110.16, Pseudomonas putida ATCC 29607, Pellicularia filamentosa IFO 6298, Penicillium rastrickii ATCC 10490, Polyporus ostreiformis CBS 36234, Staurophoma species DSM 858 and Streptomyces griseus ATCC 13273.

7. The process as claimed in claim 1 wherein, for the hydroxylation, a microorganism of one of the species Beauveria bassiana ATCC 7159 or Cunninghamella blakesleeana DSM 1906 is used.

* * * * *